(12) United States Patent
Akporiaye et al.

(10) Patent No.: US 7,288,411 B2
(45) Date of Patent: *Oct. 30, 2007

(54) PROCESS FOR SIMULTANEOUSLY EVALUATING A PLURALITY OF CATALYSTS

(75) Inventors: Duncan E. Akporiaye, Arlington Heights, IL (US); Arne Karlsson, Oslo (NO); Ivar M. Dahl, Oslo (NO); Rune Wendelbo, Oslo (NO); Kurt M. Vanden Bussche, Lake-in-the-Hills, IL (US); Gavin P. Towler, Barrington, IL (US); Ralph D. Gillespie, Gurnee, IL (US)

(73) Assignee: UOP LLC, Des Plaines, IL (US)

( * ) Notice: Subject to any disclaimer, the term of this patent is extended or adjusted under 35 U.S.C. 154(b) by 881 days.

This patent is subject to a terminal disclaimer.

(21) Appl. No.: 10/649,438

(22) Filed: Aug. 27, 2003

(65) Prior Publication Data

US 2004/0077094 A1   Apr. 22, 2004

Related U.S. Application Data

(63) Continuation-in-part of application No. 09/464,313, filed on Dec. 15, 1999, now Pat. No. 6,627,445.

(51) Int. Cl.
*G01N 31/10* (2006.01)

(52) U.S. Cl. .................. 436/37; 422/130; 422/139; 436/34; 436/155; 436/159; 436/161; 436/173

(58) Field of Classification Search ................ 422/62, 422/82.12, 99, 101–104, 129, 130, 139; 436/34, 436/37, 155, 159, 161, 173
See application file for complete search history.

(56) References Cited

U.S. PATENT DOCUMENTS 4,014,657 A   3/1977   Gryaznov et al. ........ 23/288 R (Continued)

FOREIGN PATENT DOCUMENTS

DE   198 09 477 A1   9/1999

(Continued)

OTHER PUBLICATIONS

Akporiaye, D. E.; Dahl, I. M.; Karlsson, A.; Wendelbo, R. *Angew Chem. Int. Ed.* 1998, 37, 609-611.

(Continued)

*Primary Examiner*—Arlen Soderquist
(74) *Attorney, Agent, or Firm*—Maryann Maas

(57) ABSTRACT

A process for simultaneously testing a plurality of catalysts using combinatorial chemistry has been developed. The process involves containing the plurality of catalysts in an array of parallel reactors with each reactor containing a bed of catalyst. Each bed of catalyst is then simultaneously contacted, at reaction conditions, with a reactant to form an effluent of each reactor. The reactant or an inert fluid is at a space velocity sufficient to fluidize the catalyst beds. Each of the effluents is analyzed.

25 Claims, 3 Drawing Sheets

U.S. PATENT DOCUMENTS

| | | | |
|---|---|---|---|
| 5,304,354 A | 4/1994 | Finley et al. | 422/196 |
| 5,405,586 A | 4/1995 | Koves | 422/218 |
| 5,489,726 A | 2/1996 | Huss, Jr. et al. | 585/671 |
| 5,609,826 A | 3/1997 | Cargill et al. | 422/99 |
| 5,612,002 A | 3/1997 | Cody et al. | 422/131 |
| 5,746,982 A | 5/1998 | Saneii et al. | 422/134 |
| 5,766,556 A | 6/1998 | DeWitt et al. | 422/131 |
| 5,785,927 A | 7/1998 | Scott et al. | 422/104 |
| 5,792,431 A | 8/1998 | Moore et al. | 422/134 |
| 6,063,633 A | 5/2000 | Willson et al. | 436/37 |
| 6,342,185 B1 | 1/2002 | Dahl et al. | 422/82.12 |
| 6,368,865 B1 | 4/2002 | Dahl et al. | 436/37 |
| 6,576,196 B1 | 6/2003 | Akporiaye et al. | 422/82.12 |
| 6,627,445 B1* | 9/2003 | Akporiaye et al. | 436/37 |
| 2003/0053937 A1* | 3/2003 | Akporiaye et al. | 422/99 |
| 2004/0132194 A1* | 7/2004 | Bricker et al. | 436/37 |

FOREIGN PATENT DOCUMENTS

| | | |
|---|---|---|
| WO | WO96/11878 A1 | 4/1996 |
| WO | WO97/30784 A1 | 8/1997 |
| WO | WO97/32208 A1 | 9/1997 |
| WO | WO98/07026 A1 | 2/1998 |
| WO | WO98/36826 A1 | 8/1998 |
| WO | WO98/52685 | 11/1998 |
| WO | WO99/19724 A1 | 4/1999 |
| WO | WO99/34206 A1 | 7/1999 |

OTHER PUBLICATIONS

Holzwarth, A.; Schmidt, H.; Maier, W. F. *Angew. Chem. Int. Ed.*, 1998, 37, 2644-2647.

Bein, T. *Angew. Chem. Int. Ed.*, 1999, 38, 323-326.

Taylor, S. J.; Morken, J. P. *Science*, Apr. 1998, 280( 10), 267-270.

Senkam, S. M. *Nature*, Jul. 1998, 384(23), 350-353.

Cong, P.; Doolen, R. D.; Fan, Q.; Giaquinta, D. M.; Guan, S.; McFarland, E. W.; Poojary, D. M.; Self, K.; Turner, H. W.; Weinberg, W. H. *Angew Chem. Int. Ed.* 1999, 38, 484-488.

Klien, J.; Lehmann, C. W.; Schmidt, H.; Maier, W. F. *Angew Chem. Int. Ed.* 1998, 37, 3369-3372.

Schoubye, Peter, *Journal of Catalysis*, 1969, 14, 238-216.

Rouco, A.J., *Journal of Catalysis*, 1995, 157, 380-387.

Johnson et al. *Industrial and Engineering Chemistry*, 1953, 45, 849-855.

C.J. Norton et al. Priprints O- Am. Chem. Soc. Div. Petrol. Chem. 1964, 9, 129-138.

S. Hovmand et al, Trans. Inst. Chem. Eng. 1971, 49, 149-162.

J. M. Berty in "Applied Industrial Catalysts" vol. 1, 1983, Academic Press: New York, pp. 41-67.

R. Font et al, Ind. Eng. Chem. Prod. Res. Dev. 1986, 25, 491-496.

L. Garcia et al, Energy & Fuels 1998, 139-143.

\* cited by examiner

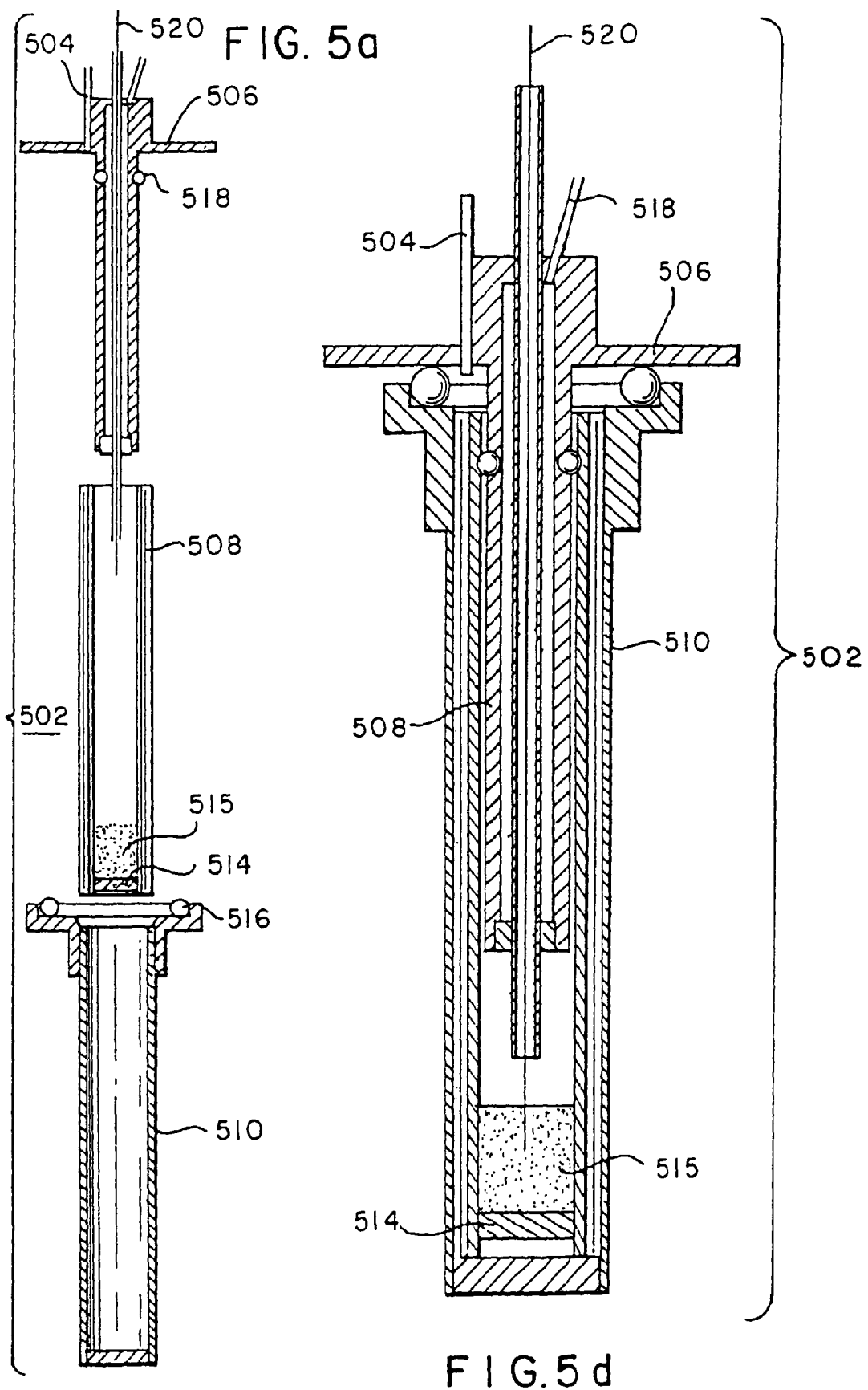

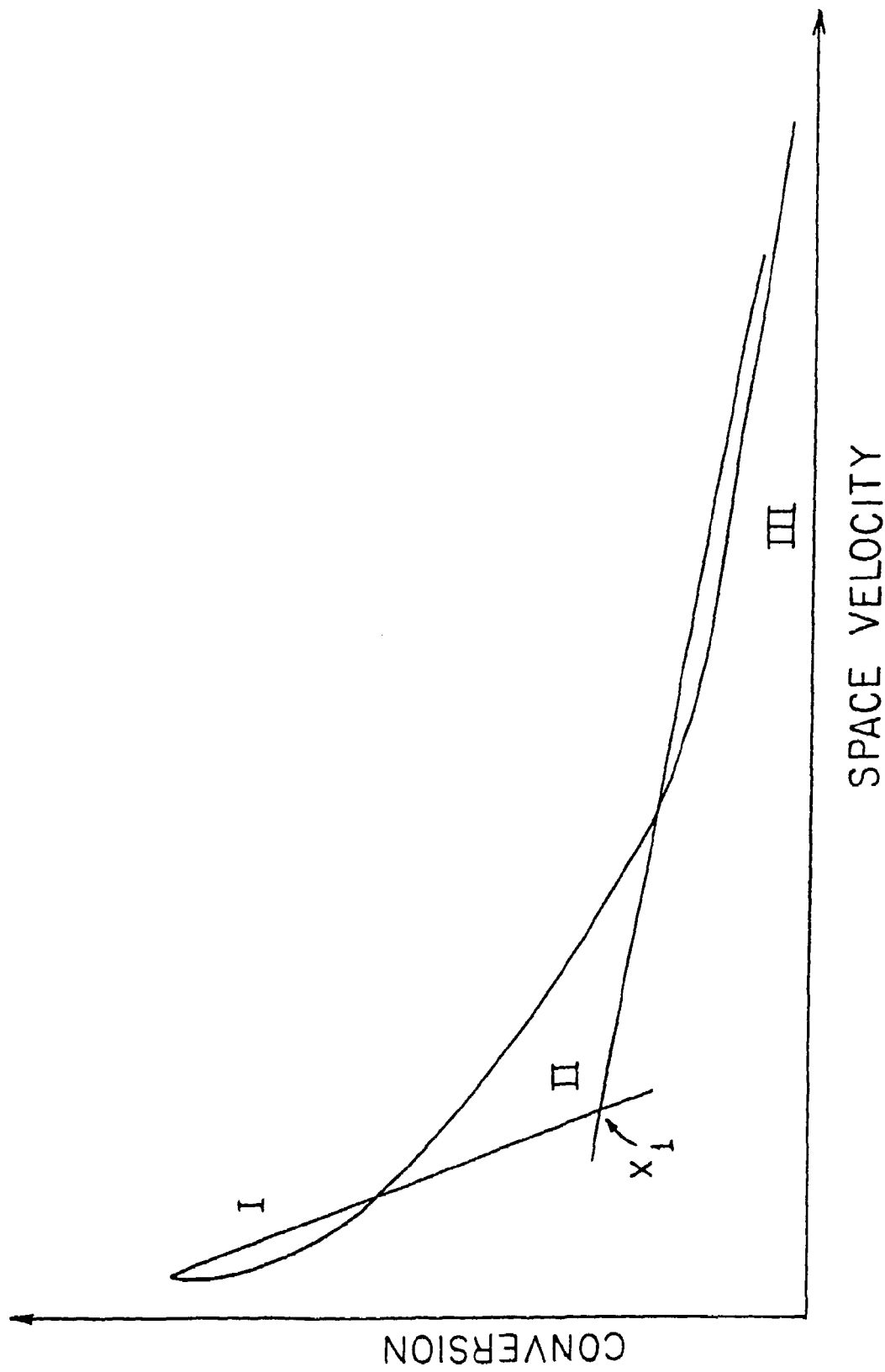

PROCESS FOR SIMULTANEOUSLY EVALUATING A PLURALITY OF CATALYSTS

CROSS REFERENCE TO RELATED APPLICATION

This application is a continuation-in-part of U.S. application Ser. No. 09/464,313 filed Dec. 15, 1999, now U.S. Pat. No. 6,627,445 which is hereby incorporated by reference in its entirety.

FIELD OF THE INVENTION

The present invention relates to a combinatorial process for simultaneously evaluating a plurality of catalysts.

BACKGROUND OF THE INVENTION

When formulating new catalysts, a large number of candidate catalyst compositions may be synthesized. It then becomes important to evaluate each of the candidate catalysts to determine the formulations that are the most successful in catalyzing the reaction of interest under a given set of reaction conditions. Two key characteristics of a catalyst that are determinative of its success are the activity of that catalyst and the selectivity of the catalyst. The term "activity" refers to the rate of conversion of reactants by a given amount of catalyst under specified conditions, and the term "selectivity" refers to the degree to which a given catalyst favors one reaction compared with another possible reaction; see *McGraw-Hill Concise Encyclopedia of Science and Technology*, Parker, S. B., Ed. in Chief; McGraw-Hill: New York, 1984; p. 854. From the activity and selectivity values, yields may be calculated, and it is advantageous to compare various catalysts based on the activity, selectivity and yields achieved.

The traditional approach to evaluating the activity, selectivity, and yield of new catalysts is a sequential one. In a microreactor or pilot plant, each catalyst is independently serially tested at one or more sets of specified conditions. In most cases, the microreactor or pilot plant is operated in a fixed bed mode. Occasionally, when the ultimate end use of the catalyst is envisioned as being in a fluidized bed application, the catalysts may be tested using a pilot plant operated in a fluidized bed mode. Upon completion of the tests at one or more sets of conditions, the current catalyst is removed from the microreactor or pilot plant and the next catalyst is loaded. The testing is repeated on the freshly loaded catalyst. The process is repeated sequentially for each of the catalyst formulations. Overall, the process of testing all new catalyst formulations is a lengthy process at best.

Developments in combinatorial chemistry have first largely concentrated on the synthesis of chemical compounds. For example, U.S. Pat. Nos. 5,612,002 and 5,766, 556 disclose a method and apparatus for multiple simultaneous synthesis of compounds. WO 97/30784-A1 discloses a microreactor for the synthesis of chemical compounds. Akporiaye, D. E.; Dahl, I. M.; Karlsson, A.; Wendelbo, R. *Angew Chem. Int. Ed.* 1998, 37, 609-611 disclose a combinatorial approach to the hydrothermal synthesis of zeolites, see also WO 98/36826. Other examples include U.S. Pat. Nos. 5,609,826, 5,792,431, 5,746,982, and 5,785,927, and WO 96/11878-A1.

More recently, combinatorial approaches have been applied to catalyst testing to try to expedite the testing process. For example, WO 97/32208-A1 teaches placing different catalysts in a multicell holder. The reaction occurring in each cell of the holder is measured to determine the activity of the catalysts by observing the heat liberated or absorbed by the respective formulation during the course of the reaction and/or analyzing the products or reactants. Thermal imaging had been used as part of other combinatorial approaches to catalyst testing, see Holzwarth, A.; Schmidt, H.; Maier, W. F. *Angew. Chem. Int. Ed.*, 1998, 37, 2644-2647, and Bein, T. *Angew. Chem. Int. Ed.*, 1999, 38, 323-326. Thermal imaging may be a tool to learn some semi-quantitative information regarding the activity of the catalyst, but it provides no indication as to the selectivity of the catalyst.

Some attempts to acquire information as to the reaction products in rapid-throughput catalyst testing are described in Senkam, S. M. *Nature*, July 1998, 384(23), 350-353, where laser-induced resonance-enhanced multiphoton ionization is used to analyze a gas flow from each of the fixed catalyst sites. Similarly, Cong, P.; Doolen, R. D.; Fan, Q.; Giaquinta, D. M.; Guan, S.; McFarland, E. W.; Poojary, D. M.; Self, K.; Turner, H. W.; Weinberg, W. H. *Angew Chem. Int. Ed.* 1999, 38, 484-488 teaches using a probe with concentric tubing for gas delivery/removal and sampling. Only the fixed bed of catalyst being tested is exposed to the reactant stream, with the excess reactants being removed via vacuum. The single fixed bed of catalyst being tested is heated and the gas mixture directly above the catalyst is sampled and sent to a mass spectrometer.

Combinatorial chemistry has been applied to evaluate the activity of catalysts. Some applications have focused on determining the relative activity of catalysts in a library; see Klien, J.; Lehmann, C. W.; Schmidt, H.; Maier, W. F. *Angew Chem. Int. Ed.* 1998, 37, 3369-3372; Taylor, S. J.; Morken, J. P. Science, April 1998, 280(10), 267-270; and WO 99/34206-A1. Some applications have broadened the information sought to include the selectivity of catalysts. WO 99/19724-A1 discloses screening for activities and selectivities of catalyst libraries having addressable test sites by contacting potential catalysts at the test sites with reactant streams forming product plumes. The product plumes are screened by passing a radiation beam of an energy level to promote photoions and photoelectrons which are detected by microelectrode collection. WO 98/07026-A1 discloses miniaturized reactors where the reaction mixture is analyzed during the reaction time using spectroscopic analysis. Some commercial processes have operated using multiple parallel reactors where the products of all the reactors are combined into a single product stream; see U.S. Pat. Nos. 5,304,354 and 5,489,726.

Applicants have developed a process to simultaneously test a plurality of catalysts in a rapid, economical, accurate, and consistent way. Applicants' invention fluidizes the multiple catalyst beds in an array of reactors so that the temperature of each catalyst bed can be accurately set, measured, and/or controlled, thereby providing for valid comparisons of catalyst performance among multiple catalysts. Applicants' invention calls for fluidization of the multiple of catalyst beds independent of whether the ultimate application of the catalyst is in a fixed bed process or in a fluidized bed process.

SUMMARY OF THE INVENTION

The purpose of the present invention is to provide a process for simultaneously testing a plurality of catalysts. The process involves containing the plurality of catalysts in an array of parallel reactors with each reactor containing a bed of catalyst. The process calls for contacting, at reaction conditions, each fluidized bed of catalyst in the plurality simultaneously with a reactant to form an effluent of each reactor. The reactant, or an inert gas, is at a space velocity sufficient to fluidize the catalyst beds. Each of the resulting effluents is analyzed.

BRIEF DESCRIPTION OF THE DRAWINGS

FIG. 5a is an exploded view of a preferred reactor.

FIG. 5d is an assembled view of the preferred reactor.

FIG. 6 is a sample plot of superficial velocity versus conversion.

DETAILED DESCRIPTION OF THE INVENTION

Figure 1:
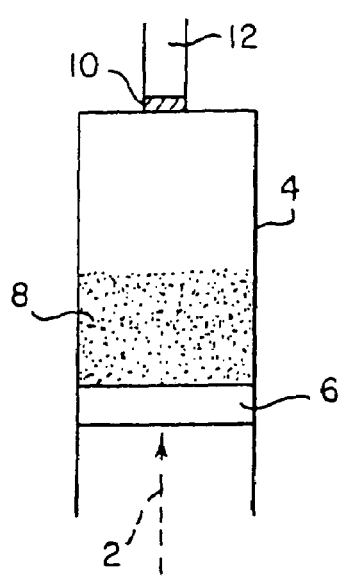
FIG. 1 is a side view of a generic fluidized bed reactor where the fluidizing gas is introduced at the bottom of the reactor.

In general terms, the present invention is a process for simultaneously testing a plurality of catalysts using a combinatorial approach that is rapid and yet provides an accurate basis for comparison of each of the characteristics determined for each of the different catalysts. The plurality of different catalysts may be any number of catalysts beginning with at least two different catalysts or a combination of catalysts. Each catalyst in the plurality may have a different formulation, or the same formulations may be present in different ratios of a mixture. Identical catalysts or mixtures may be repeated within the plurality, especially when statistical analyses are being conducted. The plurality of catalysts is contained within an array of parallel reactors with each reactor having a bed of catalyst. The array of parallel reactors may be as little as two reactors, but preferably contains 6, 8, 12, 24, 48, 96, 384, or 1264 reactors. It is most preferred that the array of parallel reactors be arranged in a row and column formation similar to that of a microtiter tray. The catalysts may be loaded into the reactors of the array, or may be formed or synthesized directly in the reactors. For purposes of the present invention, whether the catalysts are synthesized in the reactors or are loaded into the reactors after being synthesized elsewhere is not important. For overall efficiency, it may be preferable to synthesize the catalysts directly in the reactors of the array. Also for efficiency, the catalysts may be loaded into the reactors of the array simultaneously using techniques such as that described in Application Number PCT US 0312305, which is hereby incorporated by reference in its entirety. Similarly, the catalysts may be unloaded from the reactors of the array simultaneously using, for example, inversion techniques, The overall goal of the testing is to compare the yield, which is calculated from the activity and selectivity, of each of the plurality of catalysts to determine which catalyst is most suitable for a given reaction. In order to compare the yield, activity, and/or selectivity of the catalysts in the plurality, there should be a common basis for comparison. The present invention provides such a basis for comparison of the different catalysts by providing for accurate setting, measuring, and/or controlling the temperature of each catalyst bed. If the feed composition or any of the operating conditions such as pressure, space velocity, or temperature were to be unknown or inaccurate, the analytical data generated by analyzing the effluents corresponding to the plurality of catalysts would not be comparable across the array of catalyst beds. Controlling space velocity through each of the catalyst beds is accomplished through flow controllers and controlling the pressure in each of the catalyst beds is accomplished through pressure regulators. The challenge is accurately setting, measuring, or controlling the temperature in each of the catalyst beds.

The difficulty arises in that many chemical reactions are either endothermic (adsorbs heat) or exothermic (releases heat). Typically, one would set the heating means for the array of reactors at a particular temperature and pressure and then would introduce the reactants. If the reaction is endothermic or exothermic, as soon as the reactants contact the fixed bed of catalyst and the reaction begins, the temperature in the reactors will change and will no longer be at the set temperature. The amount that the actual temperature will vary from the set temperature may be different for each of the catalyst beds and will depend on the activity of the particular catalyst contained in a given catalyst bed. The greater the activity of the catalyst in a given catalyst bed, the greater the change from the set point temperature. Looking at the array of parallel catalyst beds, it is possible that each of the beds may in fact be operating at a different temperature, and none, or only some, of the beds may be operating at the set temperature. The temperature variance introduces a large amount of error into any catalyst performance comparisons made between the catalyst beds.

This effect has been used by others to estimate relative catalyst activity by using thermal imaging to monitor the temperature offsets of each of the catalyst beds. The more active catalysts would adsorb or release greater amounts of heat and change the temperature in a given catalyst bed by a greater amount. Endothermic systems are more difficult to screen. However, actual catalyst activity data as well as selectivity data are not available by the thermal imaging technique. Applicants have discovered that rapid, efficient, simultaneous testing of a plurality of catalysts is best performed where each of the catalyst beds in the array of catalyst beds is operating in a fluidized bed mode, thereby providing an accurate temperature for comparison of the analytical results obtained from the effluent of each catalyst bed. In other words, applicants have discovered that the solution to the problem of the temperature varying from catalyst bed to catalyst bed is to fluidize all the catalyst beds. All beds are fluidized without consideration as to the mode of operation in the ultimate application. That is, the present invention requires fluidization of all beds regardless of the intended mode of actual use of the catalysts in a process other than merely screening or testing.

Through fluidizing all of the catalyst beds, heat transfer is increased and, for exothermic reactions, heat is allowed to dissipate rapidly from the catalyst bed thereby preventing an increase in the temperature in the bed. For endothermic reactions, the increased heat transfer allows for continuous heating of all the catalyst particles in a bed thereby preventing a decrease in the temperature of the bed. Overall, the increase in heat transfer provided by fluidizing all the catalysts beds allows for each catalyst bed to be at its set temperature regardless of the activity of the catalyst. All the beds may be maintained at the same temperature, or individual beds may be set and maintained at different temperatures. The array may also be divided into sections with each section being operated at a different temperature. Also, heat transfer provided by fluidizing all the catalysts beds allows for isothermal conditions within each catalyst bed, i.e, a heat gradient across the bed of catalyst is not formed. In all cases, the temperature of each catalyst bed is known and therefore provides a basis of comparison for the analytical data corresponding to each of the individual catalyst beds. Catalyst activity and/or selectivity may be determined from compositional analysis of each of the effluents (discussed in detail below), and the percent yield in each of the reactors of the array may be calculated. It is preferred to compare the percent yield of the catalysts to determine which of the catalysts exhibit the most preferred performance. Catalyst deactivation trends and rates may also be determined.

Another advantage of fluidizing all the catalyst beds is to prevent or minimize any potential pressure drops across the catalyst beds. The present invention may be used with formed catalysts such as spheres and extrudates as well as unformed catalysts such as powders. It is likely that the different catalysts may have significantly different particle sizes, especially in the embodiment where the catalyst has been synthesized in the reactors of the array. In a fixed bed mode small particle sizes or fine powders may result in a restricted gas flow that could cause a large pressure drop across the reactor. Therefore, in the array of reactors the different catalyst beds may be subjected to different amounts of reactant or different pressure because of the varying restrictions of gas flow through the beds depending upon the particle size of the catalysts. Analytical results based on each of the effluents would not be comparable since each catalyst bed was exposed to a different quantity of reactant. Fluidizing all the catalyst beds solves this problem as well as the temperature problem discussed above.

The fluidizing of the catalyst beds may be accomplished by flowing gas or liquid upward through the catalyst bed. It is preferred to use the fluid reactant stream to fluidize the catalyst beds, but it is also contemplated that an inert gas or liquid stream may be used. For ease of understanding, the fluidization will be discussed in terms of a gas-solid two-phase system. The superficial or linear velocity of the fluid reactant or inert gas is controlled so that the catalyst(s) in the reaction zones are in a fluidized bed. The superficial velocity is the amount of gas fed per unit of time and unit of reactor cross sectional area. If the superficial velocity of the fluid reactant is low enough, the gravimetric force operating on the catalyst particles will be greater than the lifting or frictional force provided by the fluid reactant, and the catalyst will remain in a fixed bed resting on the fluid permeable structure attached to the sleeve. If the superficial velocity is high enough, the frictional force provided by the fluid reactant will completely overcome the gravimetric force operating on the catalyst particles, and the catalyst particles will be forced against the fluid permeable end of the reactor insert and held in a fixed bed. However, the superficial velocity of the reactant fluid may be adjusted so that the catalyst bed is fluidized. Equations to calculate the superficial velocity needed to fluidize a catalyst bed are known, $$U_{mf} = 1.118 \times 10^{-13} \times \frac{d_{p,sv}^{1.82}}{\rho_g^{0.06}} \frac{(\rho_s - \rho_g)^{0.94}}{\mu^{0.88}}$$

$$\frac{U_{mf}}{U_{mb}} = \frac{2363 \times \rho_g^{0.126} \mu^{0.523} \exp(0.716 F)}{d_{p,sv}^{0.8} g^{0.934} (\rho_s - \rho_g)^{0.934}}$$

Where:
$U_{mf}$=minimum fluidization velocity
$U_{mb}$=minimum bubbling velocity
$d_{p,sv}$=mean diameter of particles
$\rho_g$=gas density
$\mu$=viscosity
$\rho_s$=solid particle density
F=fraction of particles below 40 microns
g=gravitational constant In an application where the particle size of the catalyst is known or is measured, one of ordinary skill in the art would understand how to solve the above equations to determine the proper superficial velocity for the fluid reactant in order to fluidize the catalyst bed in the reaction zone. However, in an application where the particle size of the catalyst is not known, the standard equations above cannot be solved.

Applicants have discovered a procedure to determine the superficial velocity needed to fluidize a solid particle catalyst bed when the particle size and density of the catalyst particles are not known. The process involves ramping the superficial velocity while monitoring the conversion provided by the catalyst. All other operating conditions remain constant. FIG. 6 presents a sample graph of velocity versus conversion and shows that the curve can be divided into three regions. In Region I, the highest conversion is at the lowest superficial velocity and the conversion decreases exponentially as the superficial velocity is increased. As the superficial velocity is increased further, the slope of the curve markedly changes, i.e., becomes less negative until a plateau-like area is reached. The superficial velocity between where the slope changes substantially and where plateauing is observed is the range of superficial velocities which results in fluidization of the catalyst and is labeled Region II. As the superficial velocity becomes too great for fluidization, a fixed bed regime will again occur through pinning of the catalyst against the upper frit and the conversion is expected to decline (approaches zero) with increasing superficial velocity. This is Region III.

The curve in Region I can be approximated with a straight line (line 1) and is extended to the x-axis. The curve in Region III can also be approximated by a straight line (line 2) and extended until it meets the y-axis. The intersection of these two lines is a point having a superficial velocity ($x_1$) to whose immediate right, i.e., greater superficial velocity defines Region II where fluidization occurs.

Thus, monitoring the conversion as the superficial velocity is increased followed by a graphical analysis of the data is a method to determine the range of superficial velocities that will result in a fluidized catalyst bed. This method is preferably used in the case where the particle size of the catalyst is not known and standard equations are not sufficient. Of course, other techniques than graphical analysis of the data can be used to achieve the same result. Suitable alternatives to graphical analysis includes techniques such as mathematical modeling, numerical fitting, pattern recognition and the like. To aid in achieving proper fluidization, it is preferred that the path of fluid reactant just prior to passing through the fluid permeable structure attached to the sleeve be perpendicular to the fluid permeable structure attached to the sleeve.

In combinatorial applications, reactions are preferably conducted on a small scale. That is, while traditional fixed bed pilot plant reactions may contain from about 10 g to about 100 g of catalyst, traditional fixed bed microreactors contain from about 125 mg to about 1 g of catalyst, and traditional fluidized bed catalyst testing reactors contain about 1 g, the amount of catalyst fluidized in the present invention is preferably less than 1 g. Suitable ranges include 1 mg to less than 1 gram. The appropriate reaction conditions are dependent on the reaction being conducted. For example, for butane isomerization, temperatures include from about 150° C. to about 350° C. and pressures from about atmospheric to about 100 psig.

Figure 2:
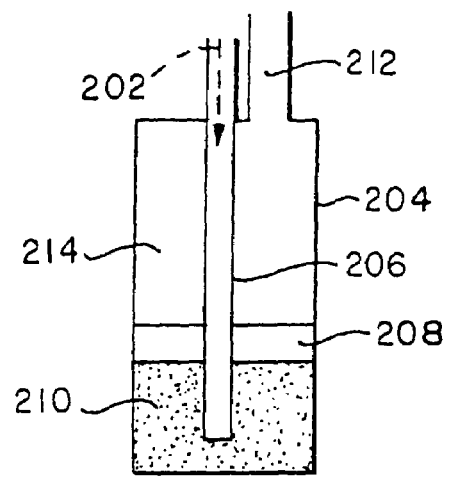
FIG. 2 is a side view of a generic fluidized bed reactor where the fluidizing gas is introduced via a conduit extending through the reactor.
Figure 3:
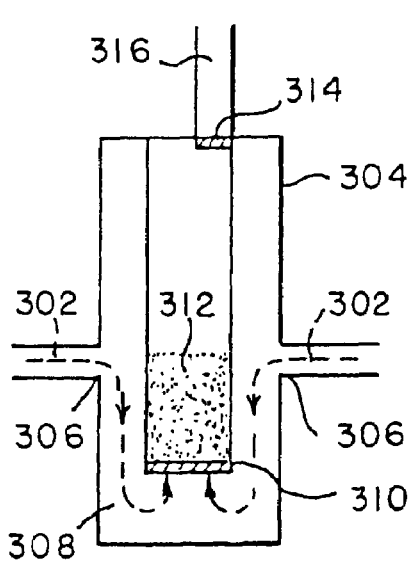
FIG. 3 is a side view of a generic fluidized bed reactor where the fluidizing gas is introduced at a side position in the reactor.
Figure 4:
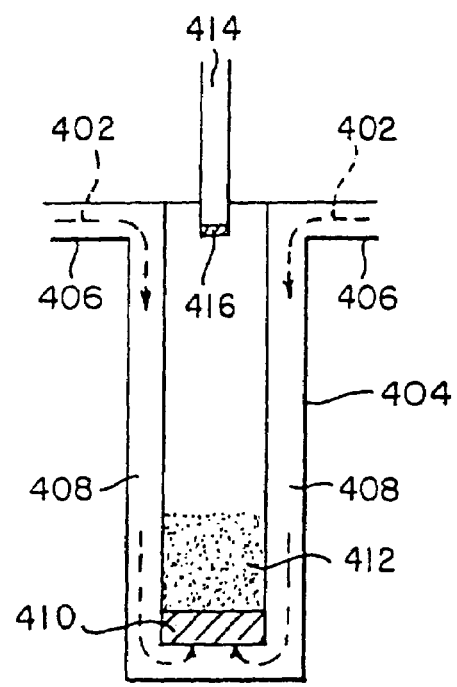
FIG. 4 is a side view of a generic fluidized bed reactor where the fluidizing gas is introduced at the top of the reactor.

FIGS. 1-4 show several different general schematics that are suitable for fluidizing the catalyst beds in the present invention. Each of the figures shows a single reactor and, in actual practice, the number of reactors may equal the number of catalysts in the array of catalysts being evaluated. FIG. 1 is the most simplistic in concept and depicts the fluidizing gas flow 2 being introduced below the reactor 4 and flowing upward through a frit 6 in the bottom of the reactor to fluidize the catalyst bed 8. Frit 10 operates to contain the catalyst within reactor 4. The effluent is removed at the top of reactor 4 via line 12. FIG. 2 shows an alternate system where the fluidizing gas flow 202 is introduced to the reactor 204 through conduit 206 which extends through reactor 204 and through frit 208 into catalyst bed 210. The effluent is removed via channel 212. Alternatively, the catalyst bed may be located above frit 208 shown as catalyst bed 214. In this alternative embodiment, channel 212 would further contain a frit (not shown) to prevent catalyst from being withdrawn from catalyst bed 214. FIG. 3 illustrates yet another embodiment where the fluidizing gas flow 302 is introduced to reactor 304 at one or more side positions 306. The gas flow travels through chamber 308 and through frit 310 into catalyst bed 312. Frit 314 operates to contain the catalyst within reactor 304. The effluent is removed via line 316. The preferred general schematic is exemplified by FIG. 4 where the fluidizing gas flow 402 is introduced to the reactor 404 through one or more conduits 406 at the top of reactor 404. The fluidizing gas travels through one or more channels 408 which extends along the inner surface of reactor 404. The fluidizing gas passes through frit 410 into catalyst bed 412. The effluent is removed via line 414. Frit 416 operates to retain the catalyst within catalyst bed 412.

Figure 5B:
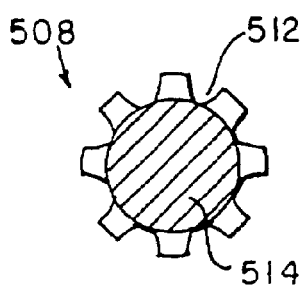
FIG. 5b is an end view of the sleeve of the preferred reactor.
Figure 5C:
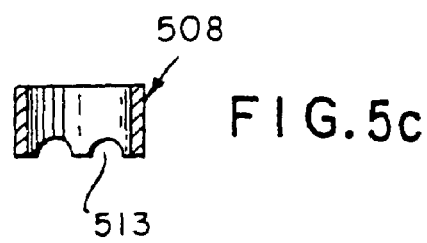
FIG. 5c is an enlarged view of the bottom end of the sleeve.

FIG. 5 illustrates the preferred reactor and fluidization scheme in greater detail. In general terms, the reactor consists of three main components, (I) a top, or reactor insert, (II) a sleeve and (III) a bottom, or well. The reactor insert fits into the sleeve which in turn fits into the well. The well is cylindrical and has a closed end at the bottom and an open end at the top. The open end of the well has a flange to retain an o-ring. The sleeve is also cylindrical with an open end at the top and a frit at the bottom. The bottom end of the sleeve is inserted into the well. The sleeve is sized so that after insertion into the well a volume is formed between the frit of the sleeve and the bottom of the well.

The reactor insert is cylindrical with a frit at a bottom end and a gas stream conduit at a top end. The top end of the reactor insert is further equipped with a flange to seal with the flange of the well via the o-ring. In one embodiment of the invention, the reactors are sealed simultaneously as described in U.S. Pat. No. 6,576,196 hereby incorporated by reference in its entirety. The top end of the reactor insert is also equipped with a conduit that extends through the flange and into a volume of space defined by the flange of the reactor insert, the flange of the well, and the outer wall of the cylinder. The reactor insert is also equipped with an o-ring at a position to seal with the top of the sleeve or an interior portion of the sleeve. The bottom end of the reactor insert is inserted into the top end of the sleeve. The reactor insert is sized so that after it is fully inserted into the sleeve, a volume is formed between the bottom of the sleeve and the bottom of the reactor insert to hold the catalyst bed.

The external surface of the sleeve and the internal surface of the well form channels through which the fluidizing gas is able to flow. Either the external surface of the sleeve or the internal surface of the well, or both, contains grooves that when the sleeve is inserted in the well define the channels. It is preferred that the grooves are located on the external surface of the sleeve and that the grooves run along the length of the cylinder as opposed to spiraling the circumference. The channels provide a path for the fluidizing gas to flow from the conduit in the flange of the reactor insert to the volume of space between the bottom of the well and the frit of the sleeve. From this volume of space, the fluidizing gas is able to pass through the frit of the sleeve and into the catalyst bed to fluidize the catalyst bed. Having channels for the fluidizing gas to flow through as opposed to simply a complete pocket between the sleeve and the well, as shown in the general FIG. 4, allows for contact and good heat transfer between the sleeve and the well along the length of the reactor. The fluidizing gas then passes through the frit at the bottom of the reactor insert and is conducted out of the reactor via the reaction insert.

Referring to FIG. 5a, FIG. 5b, FIG. 5c and FIG. 5d, the fluidizing gas enters the reactor 502 via line 504 which passes through a reactor insert 506. Reactor insert holds line 504 in the correct position relative to sleeve 508 and well 510. Well 510 holds sleeve 508 which in turn holds reactor insert 506. Sleeve 508 extends into well 510, and reactor insert 506 extends into sleeve 508. O-ring 516 seals reactor insert 506 and well 510. O-ring 518 seals reactor insert 506 and sleeve 508. Sleeve 508 is cylindrical with grooves 512 partially forming channels on the exterior circumference of the sleeve. Sleeve 508 contains frit 514 near the bottom end. The bottom end of sleeve 508 has portions removed to form channels 513. Thermocouple 520 extends through reactor insert 506 and into catalyst bed 515.

Fluidizing gas is carried from line 504 through channels formed by the grooves 512 in the exterior of sleeve 508 and the interior of well 510 and passes through frit 514. The fluidizing gas operates to fluidize catalyst bed 515, and the fluidizing gas is removed from reactor insert 506 via line 518. Reactant is added into the fluidizing gas stream and contacts the fluidized catalyst forming an effluent. The effluent is sampled via line 518 and passed to an analytical instrument for analysis.

One or more reactants are introduced to the fluidized bed in any commonly known manner. The term "reactants" is used herein to describe the process of the invention, but it should be understood that many chemical reactions require only one reactant and the use of the plural of the word reactant herein is for ease of explanation and not meant to limit the invention to only those reactions requiring more than one reactant. The present invention is successfully applied to chemical reactions having only one reactant as well as those having two or more reactants. As mentioned above, the reactants may be the gas stream that is used to fluidize the catalyst beds, or a measured concentration of the reactant may be injected into an inert gas stream that is used to fluidize the catalyst beds. Alternatively, although less preferred, the reactants may be introduced directly into the reactors independently of the gas flow being used to fluidize the catalyst beds. After being introduced in some way, as the reactants contact the catalysts a reaction may be catalyzed. Of course, since catalyst performance evaluation is the goal of the invention, it is expected that some of the catalysts tested will not catalyze the reaction at all, or perhaps only very little. When the reactants contact the catalyst beds, an effluent is formed. In the embodiment where each reactor contains a different catalyst or blend of catalysts, it is expected that the effluent may vary considerably from catalyst bed to catalyst bed. Some effluents may contain largely reactant, and others may contain largely product, with a wide variety of ratios of reactant to product possible.

The effluents produced are analyzed using at least one analytical technique to determine whether products have been formed, how much product has been formed, and/or which specific product compounds have been formed. The analytical technique used may be any suitable technique for the type of information desired and components involved. Preferred techniques include, generally, chromatography, spectroscopy, and nuclear magnetic resonance. Various different forms of chromatography and/or spectroscopy may be employed. Examples include liquid chromatography, gas chromatography, ultraviolet absorption spectroscopy, visible absorption spectroscopy, ultraviolet-visible spectroscopy, atomic absorption spectroscopy, infrared absorption spectroscopy, and emission spectroscopy. While chromatography and spectroscopy methods are preferred, other acceptable techniques include but are not limited to fluorescence spectrometry, mass spectrometry, X-ray methods, radiochemical methods, electroanalytical methods, potentiometric methods, conductometric methods, electrogravimetric methods, coulometric methods, and voltammetry.

At least a portion of the effluent from each reactor is conveyed to the analytical instrument. The effluents may be directly conducted to an analytical instrument, or aliquots of the effluents may be sampled and delivered to the location of the analytical instrument. In yet another embodiment, the effluents may be analyzed on stream as they are removed from the reactors. In evaluating catalyst performance, observing trends of activity, selectivity, and yield over time is valuable. Therefore, the effluent being withdrawn from each reactor may be periodically or continuously analyzed as discussed above. The selectivity, activity, and/or yield may be determined at each analysis time, and the trend of the selectivity and activity may then be observed over time. Similarly, catalyst deactivation may be observed, and trends and rates of deactivation may be determined. Again it is preferred that the effluents of each of the reactors be sampled simultaneously so that the analysis results are directly comparable and the time that each catalyst has been exposed to the reactant is the same. For quantitative results, the amounts of the effluents analyzed are measured.

The specific analysis performed depends upon the application and the desired information. For example, if only the activity of the plurality of catalysts are to be determined and compared, an analysis measuring the amount of reactant consumed in each effluent may be sufficient. Also, a qualitative analysis for the composition of the effluent could be used as an indication of catalyst activity. However, it is generally preferred to have both activity and selectivity information and, in that case, the analytical technique would be selected to measure the quantity of the different components present in each effluent. Using both the activity information and the selectivity information, the yield to the desired products can be calculated and compared between the individual catalysts or mixtures of catalysts that make up the plurality of catalysts.

It is preferred that the sampling of the effluent from each reaction be conducted simultaneously. The benefit of simultaneous sampling is that the results from each catalyst bed are more readily comparable since each catalyst bed would be exposed to the reactant for the same period of time. This is perhaps best described using an example. In a 48 reactor array, if the sampling of the 48 effluents were to occur sequentially, and the time needed for each sampling was one minute, there would be a 48 minute time difference between the first reactor being sampled and the last reactor being sampled. Therefore, the overall time the last catalyst would be exposed to the reactant would be 48 minutes longer than the overall time the first catalyst would be exposed to the reactant. It is known that the activity and selectivity of catalysts may change over the time the catalyst is in use. During the 48 minutes between the sampling of the first and last reactor, the activity and selectivity of the catalyst in the last reaction may have significantly changed. Sequential sampling has the likelihood of introducing error since the time the catalyst is in use would become a variable as opposed to being identical for all reactors.

What is claimed is:

1. A process for evaluating the performance of a plurality of solid particle catalysts comprising:
   a) containing the plurality of solid particle catalysts in an array of parallel reactors with each reactor containing a bed of catalyst;
   b) contacting, simultaneously, at reaction conditions and two-phase operating conditions, each bed of catalyst with at least one fluid reactant to form an effluent of each reactor;
   c) independently controlling, simultaneously, the space velocities of a plurality of fluid streams, each said stream contacting at least one associated bed of catalyst resulting in the reactors containing a fluidized bed of solid particle catalyst, wherein said fluid is selected from the group consisting of the reactant, another fluid, or a mixture thereof; and
   d) analyzing each of the effluents to determine its chemical composition.

2. The process of claim 1 wherein at least two reactors or two sets of reactors each independently have at least one associated flow control device to control fluid flow to the reactor or set of reactors.

3. The process of claim 1 further comprising loading, simultaneously, the plurality of solid particle catalysts into the array of parallel reactors.

4. The process of claim 1 further comprising unloading, simultaneously, the plurality of solid particle catalysts into the array of parallel reactors.

5. The process of claim 1 wherein each reactor comprises at least a top and a bottom, said process further comprising sealing, simultaneously, the tops and the corresponding bottoms of the array of parallel reactors.

6. The process of claim 5 further comprising unsealing, simultaneously, the tops and the corresponding bottoms of the array of parallel reactors.

7. The process of claim 1 wherein the flow of reactant introduced to each individual bed of catalyst is measured.

8. The process of claim 1 further comprising determining a characteristic of each catalyst selected from the group consisting of activity, selectivity, yield, deactivation rate, deactivation trends, and combinations thereof.

9. The process of claim 8 further comprising comparing the selected characteristic of each of the catalysts in the plurality.

10. The process of claim 1 further comprising measuring the temperature within the fluidized catalyst bed.

11. The process of claim 1 wherein the array of reactors contains a number of reactors selected from the group consisting of 6, 8, 12, 24, 48, 96, 384, and 1264.

12. The process of claim 1 wherein each effluent is analyzed by an analytic technique selected from the group consisting of spectroscopy, chromatography, nuclear magnetic resonance, and combinations thereof.

13. The process of claim 1 further comprising sampling, simultaneously, each of the effluents periodically prior to analyzing.

14. The process of claim 1 further comprising sampling, simultaneously, each of the effluents prior to analyzing.

15. The process of claim 1 wherein the effluents are continuously analyzed.

16. The process of claim 1 wherein the plurality of catalysts contains multiple different catalyst formulations.

17. The process of claim 1 wherein the beds of catalysts contain different ratios of a mixture two or more catalysts.

18. The process of claim 1 wherein the catalyst bed comprises from about 1 mg to less than one gram of catalyst.

19. The process of claim 1 further comprising, after containing the plurality of catalysts in the array of parallel reactors, ramping the superficial velocity of the reactant while monitoring the effluents to define, for each bed of catalyst, a range of superficial velocities which result in fluidization of the beds of catalyst.

20. A process for evaluating the performance of a plurality of solid particle catalysts comprising:
 a) containing the plurality of solid particle catalysts in an array of parallel reactors with each reactor containing a bed of catalyst;
 b) contacting, simultaneously, at reaction conditions and two-phase operating conditions, each bed of catalyst with at least one fluid reactant to form an effluent of each reactor;
 c) maintaining the actual temperature of the solid catalyst particles in the plurality of beds at a common desired temperature regardless of differences between beds by fluidizing each bed of catalyst using a fluid selected from the group consisting of said reactant, another fluid, or a mixture thereof; and
 d) analyzing each of the effluents.

21. A process for evaluating the performance of a plurality of solid particle catalysts comprising:
 a) containing the plurality of solid particle catalysts in an array of parallel reactors with each reactor containing a bed of catalyst;
 b) contacting, simultaneously, at reaction conditions and two-phase operating conditions, each bed of catalyst with at least one fluid reactant to form an effluent of each reactor;
 c) maintaining each catalyst bed at isothermal conditions by fluidizing each bed of catalyst using a fluid selected from the group consisting of said reactant, another fluid, or a mixture thereof; and
 d) analyzing each of the effluents.

22. The process of claim 21 wherein the isothermal conditions are substantially identical for each of the beds of catalyst.

23. The process of claim 21 wherein the isothermal conditions are different for at least two of the beds of catalyst.

24. A process for evaluating the performance of a plurality of solid particle catalysts comprising:
 a) containing the plurality of solid particle catalysts in an array of parallel reactors with each reactor containing a bed of catalyst;
 b) contacting, simultaneously, at reaction conditions and two-phase operating conditions, each bed of catalyst with at least one fluid reactant to form an effluent of each reactor;
 c) maintaining the desired pressure drop across the beds of solid catalyst particles regardless of differences between beds by fluidizing each bed of catalyst using a fluid selected from the group consisting of said reactant, another fluid, or a mixture thereof; and
 d) analyzing each of the effluents.

25. The process of claim 24 wherein maintaining the desired pressure drop across the beds of solid catalyst particles also operates to maintain the desired reactant fluid flow through the beds of solid catalyst particles.

* * * * *